US006980676B2

(12) United States Patent
Pineau

(10) Patent No.: US 6,980,676 B2
(45) Date of Patent: Dec. 27, 2005

(54) MEDICAL IMAGING SYSTEM

(75) Inventor: Pascal Pineau, Palaiseau (FR)

(73) Assignee: IODP (S.A.R.L.), (FR)

( * ) Notice: Subject to any disclaimer, the term of this patent is extended or adjusted under 35 U.S.C. 154(b) by 0 days.

(21) Appl. No.: 09/976,945

(22) Filed: Oct. 12, 2001

(65) Prior Publication Data

US 2002/0097897 A1     Jul. 25, 2002

Related U.S. Application Data

(63) Continuation of application No. PCT/FR00/00977, filed on Apr. 14, 2000.

(30) Foreign Application Priority Data

Apr. 14, 2000   (FR)   .................................... 99/04668

(51) Int. Cl.[7] .............................................. G60K 9/00
(52) U.S. Cl. ...................... 382/128; 128/922; 600/443
(58) Field of Search ................................ 382/128, 131; 600/307, 437, 447; 709/230, 231, 232; 705/2, 705/3

(56) References Cited

U.S. PATENT DOCUMENTS

| | | | |
|---|---|---|---|
| 5,432,871 A * | 7/1995 | Novik ......................... 382/232 |
| 5,482,043 A * | 1/1996 | Zulauf ........................ 128/904 |
| 5,502,726 A * | 3/1996 | Fischer ....................... 370/392 |
| 5,540,229 A * | 7/1996 | Collet-Billon et al. ....... 128/916 |
| 5,542,003 A * | 7/1996 | Wofford ...................... 382/132 |
| 5,544,649 A * | 8/1996 | David et al. ................. 128/904 |
| 5,619,991 A * | 4/1997 | Sloane ........................ 600/300 |
| 5,715,823 A * | 2/1998 | Wood et al. ................. 128/904 |
| 5,806,521 A | 9/1998 | Morimoto et al. ..... 128/661.01 |
| 5,842,473 A * | 12/1998 | Fenster et al. .............. 600/445 |
| 5,907,640 A * | 5/1999 | Delean ....................... 382/276 |
| 5,938,607 A * | 8/1999 | Jago et al. ................... 600/437 |
| 5,964,709 A * | 10/1999 | Chiang et al. .............. 600/447 |
| 5,987,519 A * | 11/1999 | Peifer et al. ................. 709/205 |
| 5,993,001 A * | 11/1999 | Bursell et al. .............. 351/212 |
| 6,241,673 B1 * | 6/2001 | Williams .................... 600/437 |
| 6,425,865 B1 * | 7/2002 | Salcudean et al. .......... 600/111 |

FOREIGN PATENT DOCUMENTS

| | | |
|---|---|---|
| EP | 0 648 469 A1 | 4/1995 |
| WO | WO 93/13916 | 7/1993 |
| WO | WO 96/17545 | 6/1996 |

\* cited by examiner

*Primary Examiner*—Samir Ahmed
(74) *Attorney, Agent, or Firm*—DLA Piper Rudnick Gray Cary US LLP

(57) ABSTRACT

An imaging system including means for transmitting a digital image, an image base, a sensor, means for referencing positions on a dummy, echographic display means, means for recalculation of a three-dimensional image, and means for receiving expert assessment results combining videoconference ability and the possibility of remote manipulation of two-dimensional images.

7 Claims, 1 Drawing Sheet

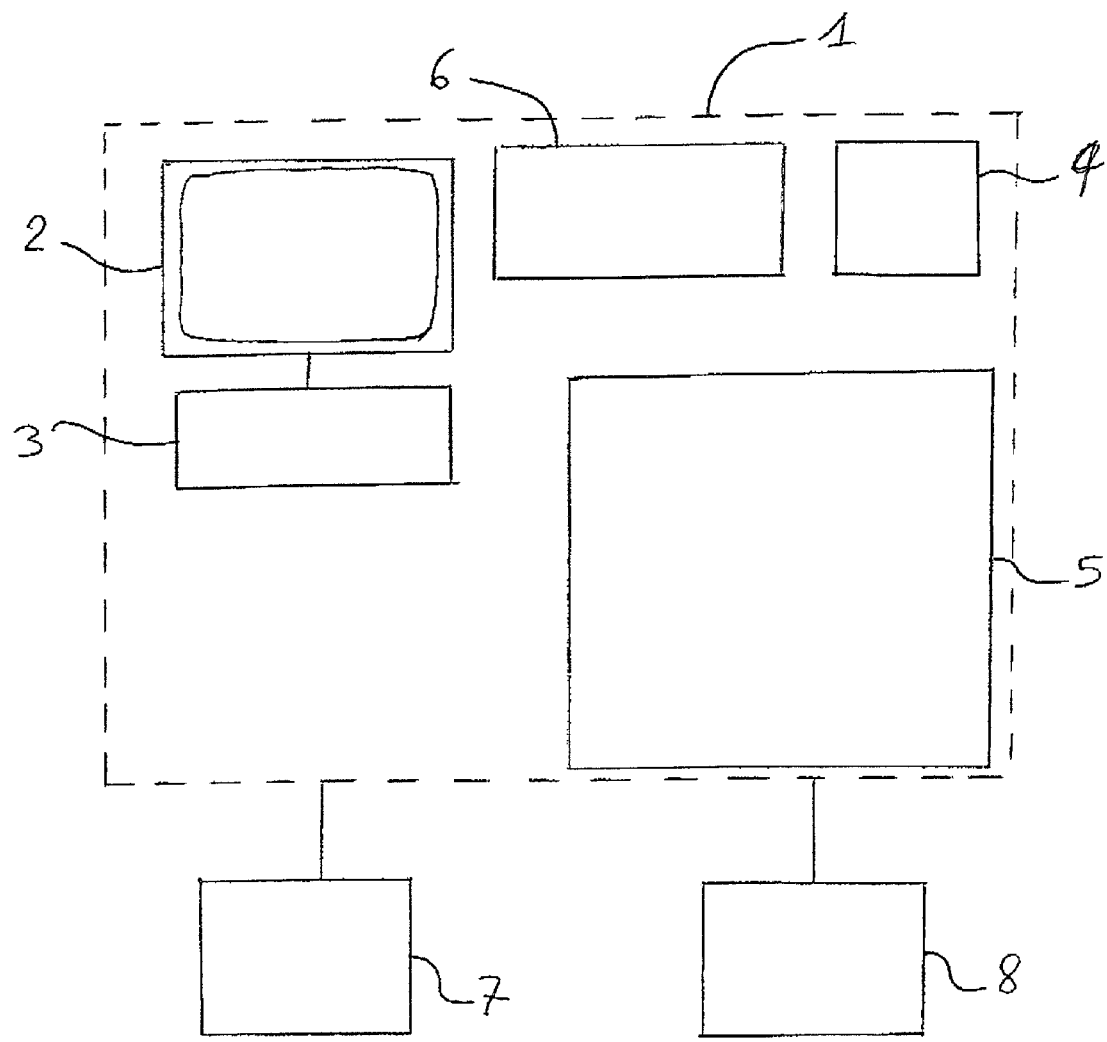

MEDICAL IMAGING SYSTEM

RELATED APPLICATION

This is a continuation of International Application No. PCT/FR00/00977, with an international filing date of Apr. 14, 2000, which is based on French Patent Application No. 99/04668, filed Apr. 14, 1999.

FIELD OF THE INVENTION

This invention concerns the field of medical imaging. More specifically, this invention concerns a remote echographic analysis system that can be used, for example, for gynecological-obstetric expert assessment.

BACKGROUND

Echography is a specific imaging modality. Good analysis of the pathological case is strongly dependent on the capacity of the technician to display a sectional plane of the patient allowing establishment of a diagnosis.

An expert assessment is often sought when the first echograph technician is not able to establish a diagnosis in a definitive manner, which is often because it was not possible to display "good" image(s). Thus, transmitting these images to an expert will not enable the expert to provide an assessment with certainty.

In contrast, if the expert is given the possibility of performing the examination on a volumic data block, it will be possible to display the sectional planes required for the diagnosis. This analysis can be performed during the preparation of the coordination meeting, without particular limitation: the data to be analyzed are accessible, they can be analyzed by multiple experts, duplicated, transmitted or printed.

During the coordination meeting, the expert can show the images that he obtained and, by means of interactive remote manipulation of the data block, show the manner in which to display them.

Thus, there is a double benefit: a real expert assessment with an efficacy at least doubled compared to sending a file composed of several fixed images and a training activity because the expert explains the manner in which the pertinent images are obtained.

SUMMARY OF THE INVENTION

This invention relates to an imaging system including means for transmitting a digital image, an image base, a sensor, means for referencing positions on a dummy, echographic display means, means for recalculation of a three-dimensional image and means for receiving expert assessment results combining videoconference and the possibility of remote manipulation of two-dimensional images.

BRIEF DESCRIPTION OF THE DRAWING

The drawing is a schematic layout of a system in accordance with aspects of the invention.

DETAILED DESCRIPTION

The invention is based on the manipulation of a volumic echographic information base. The first step of the process is the acquisition of these data. The invention makes it possible to constitute a volumic data base on a zone to be analyzed, to transmit it to an expert site, to analyze it reproducing the echographic exploration movements, then to communicate the expert assessment in an enhanced videoconference type exchange.

The invention concerns an imaging system comprising means for transmitting a digital image, an image base, a sensor and means for referencing positions on a dummy, as well as echographic display means, means for recalculation of a three-dimensional image and means for receiving expert assessment results combining videoconference and the possibility of remote manipulation of two-dimensional images.

The invention also concerns a station for the acquisition of a three-dimensional image, its transfer for implementation of a system comprising means for linking multiple physical devices.

As shown in the drawing, the workstation 1 is advantageously constituted of:
- a central unit 3,
- a display screen 2,
- a high-definition digitalization card 4 enabling acquisition of an echograph video signal,
- a three-dimensional position sensor 6 giving the spatial positions of the echographic probe 7, and
- videoconference means 5 integrating an electronic card and a two-way video input, a color camera, a microphone and a headset.

The station 1 is connected at one side to the echograph 7 and on the other to a communication/ISDN network 8, with the station comprising means for temporarily storing the data acquired from the echograph until they are transmitted to the expert then exploited in the videoconference.

The invention also concerns a workstation for implementation of a system intended to receive a file for expert assessment, performance of the virtual echographic examination (display of any sectional planes from the three-dimensional matrix), transmission of the electronic report and hosting a session of receiving expert assessment combining videoconference and remote manipulation of the three-dimensional matrix.

The workstation preferably comprises a central unit, a screen, a three-dimensional position sensor giving the spatial positions of the virtual echographic probe, a videoconference kit combining an electronic card and a two-way video input, a color camera, a microphone and a headset, a reproduction bank and a color ink-jet printer.

Acquisition is implemented from any echograph: an acquisition station is connected to the standard video output (preferably S-VHS) and enables recording of the echographic data obtained by scanning of the zone to be studied.

A three-dimensional position sensor located on the standard probe makes it possible to record with great precision the position in space of the planes acquired, which makes it possible to construct a volumic image of the zone studied.

An original process processes the acquired planes and produces a volumic base of high quality. Acquisition of the echographic data can be performed under different angles making it possible, in particular, to limit the effects of shadow cones. A specific data acquisition protocol for each organ or zone to be analyzed allows optimization of the data collection at the source. The echograph technician needs only to follow this protocol to be assured that sufficient data have been recorded to enable a differential diagnosis.

Acquisition of the source data can also be implemented in synchronization with physiological signals, e.g., the EKG. This technique makes it possible to only conserve the echographic data synchronous with an instant of the cardiac cycle (case of vascular analysis).

Transfer of the Data

The acquired volumic data are stored in the acquisition station in the form of a data file which can be transferred to the expert center via any digital channel: removable magnetic support, local network, modem, ISDN connection and the like.

Analysis by the Expert

An expert uses a diagnostic station compatible with the acquisition system and has available tools allowing him to display the collected data.

The display principle is simple: a virtual probe, connected to the expert's station, allows the expert to select the two-dimensional plane to be displayed in the three-dimensional echographic matrix. The image is displayed on a screen in a format equivalent to that of an echograph. Functions of the contrast/brightness adjustment type, and simple functions of annotation and measurement complete the interface.

When the expert displays the image of interest, it can be saved for printing or transmission. The expert assessment file is constituted in this manner.

Receiving the Expert Assessment

The acquisition (collection center) and expertise stations comprise a simple video conference type function with a window in the screen allowing display of the image of the interlocutor. One channel allows the dialogue.

During submission of the expert assessment conclusions, the electronic file comprising multiple images and the associated comments is transmitted from the expert to the collector. These static data are those upon which the diagnosis was established.

As a complement to this file and oral comments, the expert can manipulate the three-dimensional matrix of the echographic data that was analyzed and present in parallel on the expert's screen and on the screen of the collector center the selected sectional planes, thereby implementing in real time a virtual echographic exploration, with high added pedagogical value. Since the three-dimensional matrices are available at both sites, it is only necessary to transmit from one site to the other the control data for selecting the sectional plane to be displayed.

A derivative application of this technology is that it is possible to record these control data and thus to replay the entire examination by recording a minimum of data.

The Protection

External Context

Known in the prior art is a training system based on the trainer's station (image base, probe, positional referencing on a dummy, echographic type display) but also including the source data acquisition phase.

The invention is differentiated from the prior art essentially by the fact that:

capturing of images and constitution of the three-dimensional matrix: concept of "new image" enabling display of more details than contained in a single two-dimensional image, receiving the expert assessment combining the videoconference and the possibility of remotely manipulating the two-dimensional images: the contribution in terms of quality of the rapport and its pedagogical strength is very strong.

The Architecture of the Collecting Station

The architecture of the proposed station implements the functionalities required for the acquisition of a three-dimensional image, its transfer and inclusion in a videoconference subsystem. Depending on the local context, these functionalities can be supported by one or more physical devices. In fact, depending on the task organization in the medical structure, it can be of value to separate or consolidate the functions of videoconference interface and echographic data acquisition (requiring an immediate proximity of the echograph).

The description below is based on the assumption that all of the functions are consolidated on the same device.

The workstation is constituted of:
- a PC type central unit with the following minimal configuration: Pentium IT 400 MHz operating under Windows NT, 128 MB of memory, 4.3 GB disk, keyboard, mouse,
- a 17" display screen,
- a high-definition digitalization card enabling acquisition of the echograph video signal,
- a three-dimensional position sensor giving the spatial positions of the echographic probe,
- a videoconference kit integrating a PCI card supporting H320 standards up to 384 Kbits/sec and H323 and a two-way video input, a color camera, a microphone and a headset.

The station is connected on one side to the echograph and on the other to the ISDN network. It allows temporary storage of the data acquired from the echograph until they are transmitted to the expert, then exploited during the videoconference.

The Architecture of the Expert's Station

The expert's station makes it possible to receive a file for expert assessment, performance of the virtual echographic examination (display of any sectional planes from the three-dimensional matrix), transmission of the electronic report and hosting a session of receiving expert assessment combining videoconference and remote manipulation of the three-dimensional matrix.

The workstation is constituted of:
- a PC type central unit with the following minimal configuration: Pentium IT 450 MHz operating under Windows NT, 128 MB of memory, 9 GB disk, keyboard, mouse,
- a 21" display screen,
- a three-dimensional position sensor giving the spatial positions of the virtual echographic probe,
- a videoconference kit integrating a PCI card supporting H320 standards up to 384 Kbits/sec and H323 and a two-way video input, a color camera, a microphone and a headset,
- a reproduction bank,
- a color ink-jet printer.

The Interface Between the Two Stations

The stations are connected to the ISDN network. The number of channels used is directly linked to the anticipated performance in terms of data transfer (echographic matrix and videoconference). The use of six channels gives optimal results.

What is claimed is:

1. An imaging system comprising:
   an acquisition workstation comprising:
   means for acquiring an echographic image and generating a digital image formed by a three-dimensional matrix from echographic sectional planes of said echographic image;
   means for transmitting a two dimensional section of said digital image to a diagnostic workstation in response to manipulation of a probe disposed at the diagnostic workstation, said diagnostic workstation disposed remotely from a subject;

said diagnostic workstation comprising:
said probe and means for referencing positions on a dummy;
echographic display means connected to the means for referencing positions;
means for performing a virtual echographic examination of said digital image with said probe to select any two-dimensional sectional plan from said digital image;
means for expert assessment including a module for permitting the transfer of interactive audio and visual content between the acquisition workstation and an expert at the diagnostic station; and
means for transmitting control data between said acquisition workstation and said diagnostic workstation, said control data allowing a user to select, on each workstation, a sectional plan to be visualized.

2. A workstation on comprising:
means for acquisition of a three-dimensional image;
means for processing said three-dimensional image in the system according to claim 1, wherein said acquisition workstation comprises:
means for communicating with the diagnostic workstation to display at the same time on the screen of said diagnostic workstation and on the display of said acquisition workstation sectional planes selected by the expert performing in real time a virtual echographic probe from the three-dimensional matrix available on the acquisition and diagnostic workstations, said means transmitting from one workstation to another station only said control data allowing for selection of the sectional plane to be visualized; and
means for recording said control data and again performing an examination.

3. The workstation for the acquisition and processing of a three-dimensional image according to claim 2, comprising:
central unit,
display screen,
high-definition digitalization card enabling acquisition of an echograph video signal,
a three-dimensional position sensor giving spatial positions of the echographic probe,
videoconference means integrating an electronic card and a two-way video input, a color camera, a microphone and a headset,
means for connecting to a communication network and an echograph, and
means for temporarily storing data acquired from the echograph until transmitted to a selected recipient then exploited in the videoconference.

4. A workstation for implementation of the system according to claim 1, adapted to receive a file for expert assessment, performance of a virtual echographic examination, transmission of an electronic report and hosting a session of receiving expert assessment combining videoconference and remote manipulation of the three-dimensional matrix.

5. The workstation according to claim 4, comprising a central unit, a screen, a three-dimensional position sensor giving spatial positions of a virtual echographic probe, a videoconference kit combining an electronic card and a two-way video input, a color camera, a microphone and a headset, and a color jet printer.

6. A workstation comprising:
means for acquisition of a three-dimensional image;
means for processing said three-dimensional image in a system according to claim 1; and
means for linking multiple physical devices.

7. The workstation accord to claim 2, which comprises;
central unit,
display screen connected to the central unit,
high-definition digitalization card enabling acquisition of an echograph video signal associated with the central unit,
a three-dimensional position sensor giving spatial positions of the echographic probe associated with the central unit,
videoconference means integrating an electronic card and a two-way video input, a color camera, a microphone and a headset,
means for connecting to a communication network and an echograph, and
means for temporarily storing data acquired from the echograph until such data is transmitted to an expert present in a videoconference.

* * * * *